United States Patent [19]

Heiland et al.

[11] 4,017,792
[45] Apr. 12, 1977

[54] DEVICE FOR DETERMINING AND/OR MEASURING ALCOHOL CONTENT IN A GAS AND METHOD OF MANUFACTURING A SEMI-CONDUCTOR BODY FOR USE IN ALCOHOL DETECTION

[75] Inventors: Gerhard Heiland; Claus Dieter Kohl, both of Aachen, Germany

[73] Assignee: Dragerwerk Aktiengesellschaft, Germany

[22] Filed: Sept. 2, 1975

[21] Appl. No.: 609,551

[30] Foreign Application Priority Data

Sept. 5, 1974 Germany .................. 2442593

[52] U.S. Cl. .................. 324/71 SN; 73/27 R; 338/34; 338/22 SD; 23/254 E; 340/237 R
[51] Int. Cl.² .................. G01N 57/00; H01C 7/00; G01N 37/00
[58] Field of Search ............ 324/71 SN; 340/237 R; 73/27 R, 23; 338/34, 22 SD; 23/254 E, 232 F

[56] References Cited

UNITED STATES PATENTS

| | | | |
|---|---|---|---|
| 3,547,835 | 12/1970 | Short | 338/22 SD |
| 3,695,848 | 10/1972 | Taguchi | 23/254 E |
| 3,699,803 | 10/1972 | Sumi et al. | 73/27 R |
| 3,732,519 | 5/1973 | Taguchi | 338/34 |
| 3,818,899 | 6/1974 | Venema | 340/237 R |

Primary Examiner—Rudolph V. Rolinec
Assistant Examiner—Vincent J. Sunderdick
Attorney, Agent, or Firm—McGlew and Tuttle

[57] ABSTRACT

A sensor for determining and/or measuring alcohol which exhibits an electric conductivity which varies with the alcohol concentration, comprises a heater with a metallic-oxide semi-conductor body located in the range of the heater. A pair of opposite polarity electrodes are biased into engagement with the surface of the body by a spring clamping means. The semi-conductor body comprises a zinc oxide having a density which is close to the density of a monocrystal. The semi-conductor body is formed of zinc oxide and then sintered at a temperature above 750° C and preferably at 1000° C.

9 Claims, 3 Drawing Figures

DEVICE FOR DETERMINING AND/OR MEASURING ALCOHOL CONTENT IN A GAS AND METHOD OF MANUFACTURING A SEMI-CONDUCTOR BODY FOR USE IN ALCOHOL DETECTION

FIELD AND BACKGROUND OF THE INVENTION

This invention relates in general to the constuction of a gas sensor and to a method of manufacturing a zinc oxide semi-conductor for such sensor and, in particular, to a new and useful sensor having a metallic semiconductor arranged in a gas stream formed by a casing which is adapted to be heated and wherein electrodes of respective polarity are connected to respective ends of a metallic oxide semi-conductor which is formed of zinc oxide and then sintered at a temperature above 750° C.

DESCRIPTION OF THE PRIOR ART

The present invention relates particularly to sensing devices for determining and measuring alcohol content in a gas stream, such as the breathing air of a person. It is known that metallic-oxide semi-conductor materials, such as $SnO_2$, $ZnO$ and $Fe_2O_3$, absorb reducing gases, such as hydrogen and carbon monoxide, and therefore, change their electric conductivity. Another group of metallic-oxide semi-conductor materials, such as $NiO$ and $Cr_2O_3$, change their electric conductivity at the absorption of oxidizing gases. In any case, the variation of the electric conductivity is a measure of the presence oand concentration of the gas to be determined.

In a known gas-detection element, an additional metal is used in the semi-conductor material to influence the conductivity in the direction of greater sensitivity, and gold is provided as the additional metal. Gold, however, may diffuse during the heating and influence the conductance of the metallic oxide in an undesirable manner and it will be an irreversible influence. Moreover, the semi-conductor material which forms the gas-detection element is surrounded by a porous material, such as asbestos, glass fibers or cement. Such gas-detection elements do not permit a satisfactory separation of alcohol and water and, thereby, the measuring of alcohol in the presence of water. In addition, the measuring currents which vary from 10 to 50 $\mu A$ are very small and, therefore, require sensitive measuring instruments. The porosity of the sintered body and its envelope which is complicated to manufacture make the measuring a slow operation.

Another known gas-detector is formed by a body which comprises a semi-conducting metallic-oxide having an electric resistance which varies with the absorption of gas or smoke. Silicone dioxide or silicagel is added into the body of the metallic oxide so that the diminution of the absorbing surface which occurs during the sintering of the body will be prevented and, at the same time, the mechanical resistance is to be increased. Since the admixtures are an additional structure material, the electrical resistance is increased and the gas-detector furnishes only a small measuring current. (approximately 50 $\mu A$) This means that very sensitive measuring instruments are necessary.

Another gas-detection device comprises a metallic-oxide semi-conductor element which contains at least one further metal in its crystal-lattice structure. The added metal is platinum in the amount of up to 3%. In addition, further combinations are suggested, including zinc oxide with platinum and gallium, ferrous oxide with tin, and also, lithium, and ferric oxide with thallium. The temperature of the semiconductor most favorable for the absorption of the gas to be detected is obtained by means of an embedded heating element. In one of the combinations is there a separation of alcohol from water or water vapor which is satisfactory. The firmly embedded heating element does not heat the semiconductor uniformly and this applies also to the gas-detection element mentioned previously. The result is that the measured value is neither sufficiently reproducible nor sufficiently accurate.

For connection and output of the measuring current, all of the known gas-detection devices comprise a metallic-oxide semi-conductor element with precious metal electrodes. During the manufacture of the semi-conductor element, these electrodes are subjected to the sintering operation at the same time. No reliable contact can be obtained with electrodes secured in this manner. This becomes understandable in considering the unequal thermal expansion coefficients of the metallic-oxides and the electrode material. This results in hairline cracks and high contact resistances.

SUMMARY OF THE INVENTION

The present invention provides a sensor for determining and/or measuring alcohol which ensures a short measuring time and a high sensitivity. The measuring accuracy and the reproducibility of the accuracy, even in the presence of water vapor, is very high and the instrument is of rugged construction capable of being used as a hand instrument or a portable measuring device.

In accordance with the invention, the metallic-oxide semi-conductor body is located within a heating device and it is made of a zinc oxide having a density which is close to the density of a monocrystal. Contact of the connecting electrodes with the metallic-oxide semi-conductor body is effected by pressing the electrodes against the surface of the semi-conductor body by use of an encircling clamp which engages and presses the electrodes against the body from respective opposite ends thereof.

The invention provides a very sensitive instrument such that with the same alcohol concentration, the sensing elements have a sensitivity which is increased by approximately a factor of 50 and the sensitivity to water vapor remains almost the same. Very advantageous is the linear dependence of the maximum slope $I_{max} = dI/dt$ of the measured value on the alcohol concentration. Due to this dependence, the measuring time can be very short without affecting the accuracy.

The reliability of the measurement is ensured, in addition, by the connecting of the electrodes by a clamp which presses them into contact with the semiconductor body. As compared to the construction in which the electrodes are subjected to a sintering operation, the electrodes of the inventive construction have the great advantage inasmuch as substantially perfect contact is maintained after considerable temperature variations and at high operational temperatures of about 400° C. The sintered electrodes, on the contrary, because of possible hairline cracks in the semiconductor material, may produce additional contact resistances which are uncontrollable in the measuring operation. The electrodes in pressure contact are securely electrically connected to the semi-conductor body under stronger mechanical stresses. Thereby, they meet a requirement which is a matter of course for portable measuring devices.

The advantageous location of the metallic semi-conductor body within the heating device ensures a uniform temperature which, in view of the objective, results in a very high accuracy of measurement. Very effective and, at the same time, very advantageous is another development of the invention which provides carbon electrodes. Such electrodes make sure a uniform contact over a longer period of operational time without leaving disturbing reaction products. Electrodes pressed against the metallic-oxide semi-conductor body by spring-force ensure a low contact resistance even at high operational temperatures.

For using the sensing element under a heavy load of water vapor, it is useful to keep the metallic semi-conductor body within a heating device at a relatively high temperature, for example, of 400° C. In a particular embodiment, the metallic-oxide semi-conductor body is made of zinc oxide with an admixture of silver in a quantity of up to 2.4% by weight of the zinc oxide. The silver admixture makes the conductivity, relative to the alcohol, less dependent on water vapor and the incandescent light-radiation of the heating device.

The inventive sensor as a whole differs surprisingly from the known devices in its high accuracy and extremely short measuring time and, therefore, its capability of providing a rapid succession of individual measurements. The device is rugged and very reliable in operation even after a long service time.

The method of manufacture of the metalic-oxide semiconductor body in a securely reproducible manner provides, in accordance with the invention, that the semi-conductor body is first formed of a powder of zinc oxide and it is then sintered at a temperature above 750° and, preferably, at approximately 1000° C. When the zinc oxide is also combined with silver, the components of the zinc oxide powder and a pulverulent silver compound are mixed with each other prior to forming the semi-conductor body and then the body is formed and sintered at a temperature above 750° C, preferably at 1000° C. Due to this method, a semi-conductor body is obtained having a density which is close to the density of a monocrystal. The body is stable and not brittle. Its surface is of a nature such that the sorption processes take place in a very effective manner. This applies both to the magnitude of the conductivity and to the velocity of its variation.

For the use of the inventive sensor in an alcohol measuring operation, the measured quantity is the increase in time of the current which flows through the metallic-oxide semi-conductor body under a constant applied voltage. The provided arrangement reduces the time from the intake of the gas to be measured to the reading of the measured value and to the determination of the alcohol concentration. The same also applies to the time of regeneration of the semiconductor body. In the shortest time, the body is again ready for the next measuring operation.

Accordingly, it is an object of the invention to provide a sensor for determining or measuring alcohol which comprises a metallic-oxide semi-conductor body which is advantageously arranged within a tubular heater and which is engaged by a pair of opposite polarity electrodes, preferably by clamping means, and wherein, the metallic-oxide comprises a zinc oxide having a density which is close to the density of a monocrystal.

A further object of the invention is to provide a method of manufacturing the semi-conductor body wherein, the body is formed of a zinc oxide which is sintered at a temperature of above 750° C.

A further object of the invention is to provide a device for measuring alcohol content, particularly in a persons's breath, which is simple in design, rugged in construction and economical to manufacture.

The various features of novelty which characterize the invention are pointed out with particularity in the claims annexed to and froming a part of this disclosure. For a better understanding of the invention, its operating advantages and specific objects attained by its uses, reference should be had to the accompanying drawings and descriptive matter in which there are illustrated preferred embodiments of the invention.

DESCRIPTION OF THE PREFERRED EMBODIMENTS

Figure 1:
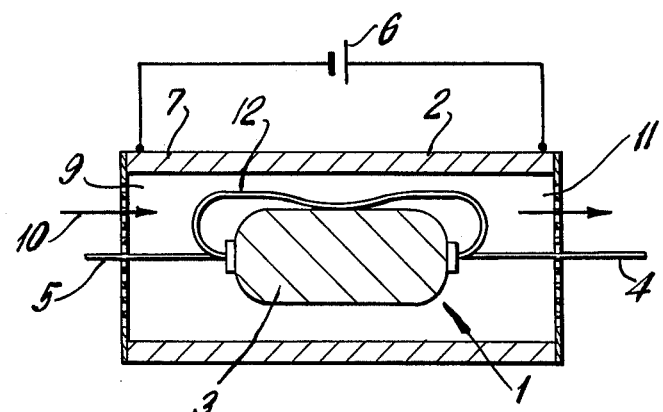
FIG. 1 is a transverse sectional view through a device for testing for alcohol content of a person's breath constructed in accordance with the invention.

Referring to the drawings in particular, the invention embodied therein in FIG. 1, comprising an alcohol testing device, for example, which may be connected to a person's breathing by a connecting tube or mouthpiece and which includes an alcohol sensor, generally designated 1, which comprises a metallic semi-conductor body 3, located within a breathing gas flow stream within a tubular member which is advantageously formed as a tubular heater 2.

In accordance with the invention, the metallic-oxide semi-conductor 3 is connected at respective opposite ends by opposite polarity electrode pairs 4 and 5. The electrodes are advantageously clamped in position by a spring clamp 12 which encircles one side of the metallic-oxide semi-conductor body 3.

Tubular heater 2 advantageously comprises a metallic wall 7 heated by a battery 6 in the manner of an electric resistance heater. The gas, such as a person's breath, is supplied, for example, through a mouthpiece (not shown) to an inlet end 9 in the direction of the arrow 10 and over the metallic-oxide semi-conductor body 3 and out an outlet 11 at the opposite end. In accordance with a feature of the invention, the metallic-oxide semi-conductor body 3 is made of a zinc oxide and, if desired, it includes an admixture of silver. It is formed in accordance with the invention by sintering such that the zinc-oxide semi-conductor body 3 achieves a density which is close to the density of a monocrystal. The connecting electrodes 4 and 5 are carbon electrodes. In the preferred operational procedure, the heater casing 7 is heated by the battery 6 to an operating temperature within the tubular casing 7 of about from 400° to 500° C.

Figure 2:
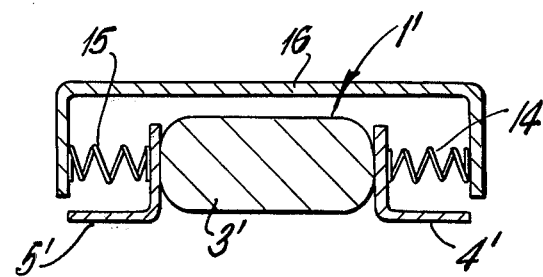
FIG. 2 is a view similar to FIG. 1 of another embodiment of the invention.

In the embodiment of the invention shown in FIG. 2, there is a sensor, generally designated 1', which comprises a metallic semi-conductor body 3' which is covered on only one side by a U-shape stirrup 16. The electrode pairs 4' and 5' are held against the metallic oxide body 3' by means of springs 14 and 15, respectively, which are biased between the electrodes and the end flanges of the stirrup 16.

Figure 3:
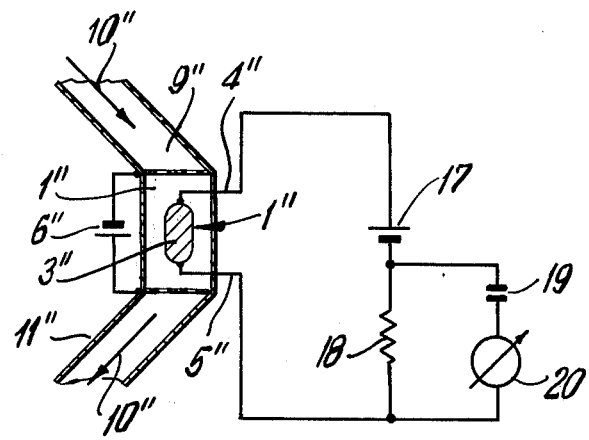
FIG. 3 is a circuit diagram of a gas-detection device of another embodiment of the invention.

In the embodiment shown in FIG. 3, a sensor 1″ is similar to the sensor shown in FIG. 1, and it includes a metallic oxide body 3″, which is connected electrically through a battery 17. Sensor 1″, including the metallic oxide body 3″, is connected by a connecting electrode 4 to one pole of battery 17 and its opposite electrode 5″ is connected to the other pole of the battery. In addition, a capacitor 19 and a measuring instrument 20 are arranged in parallel to a resistance connected between electrode 5″ and battery 17. The parallel connection of resistance 18 and capacitor 19 constitutes a differentiating network. The measuring instrument 20 indicates the derivative with respect to time $I_{max} = dI/dt$ of the current flowing through the metallic-oxide semiconductor body 3″. With a constant voltage of batter 17, the current is determined by the variation of the conductivity of the metallic-oxide semi-conductor body 3″ in the presence of alcohol in the gas to be measured.

Due to the linear dependence of the slope (derivative with respect to time) on the gas-vapor concentration, it is sufficient to measure the rise and this can be done after some few seconds. This results in a short measuring time.

The other portions of the device, including the tubular member 7″ which functions as a heater under the control of a battery 6″ is similar to that shown in FIG. 1.

While specific embodiments of the invention have been shown and described in detail to illustrate the application of the principles of the invention, it will be understood that the invention may be embodied otherwise without departing from such principles.

What is claimed is:

1. An alcohol presence sensor, comprising a conduit for the passage of breathing air therethrough, a heater carried by said conduit for heating the space within said conduit, a metallic oxide semiconductor body disposed within said conduit and spaced inwardly from the interior thereof so that breathing air passing through the conduit may pass thereover, said metallic oxide semiconductor body being made of zinc oxide and having a density approximating the density of a monocrystal, first and second electrodes of respective opposite polarity engaging respective opposite ends of said body, clamping means engaged with each electrode and applying a high clamping bias against each electrode to said body to establish said biased connection to said body, and indicating circuit means connected to said electrodes responsive to variations in the resistance of said body and to the variations of breathing air produced by the presence and absence of alcohol to indicate such variations.

2. An alcohol presence sensor according to clam 1, wherein said clamping means comprises a seat clamp extending around a side of said body and over each end into engagement with the respective first and second electrodes.

3. An alcohol presence sensor according to claim 1, wherein said clamping means includes a spring biased against each electrode.

4. An alcohol presence sensor according to claim 1, wherein said circuit means includes a differentiation network connected between said first and second electrodes, said network including a measuring instrument and a battery.

5. A sensor according to claim 1, wherein said electrodes are carbon electrodes.

6. A sensor according to claim 1, wherein said clamping means comprises a spring.

7. A sensor according to claim 1, wherein said metallic-oxide semi-conductor body comprises a zinc oxide with an admixture of silver in a quantity of up to 2.4% by weight of zinc oxide.

8. A sensor according to claim 1, wherein said heater comprises a tubular member defining said conduit and a gas flow passage therein, said metallic-oxide semiconductor body being located in said flow passage, said flow passage having an inlet and an outlet for the air to be examined.

9. A sensor according to claim 8, wherein said heater comprises a tubular member forming a resistance heater and a battery connected to said tubular member for heating said member.

* * * * *